United States Patent

Blumenfeld et al.

[11] 4,147,881
[45] Apr. 3, 1979

[54] TETRABROMOXYLYLENE DIACRYLATES AND SUBSTITUTED ACRYLATES

[75] Inventors: Georg Blumenfeld, St. Augustin; Egon N. Petersen, Neunkirchen; Hermann Richtzenhain, Much-Schwellenbach; Wilhelm Vogt, Cologne; Norbert Vollkommer, Troisdorf, all of Fed. Rep. of Germany

[73] Assignee: Dynamit Nobel Aktiengesellschaft, Troisdorf Bez. Cologne, Fed. Rep. of Germany

[21] Appl. No.: 715,954

[22] Filed: Aug. 19, 1976

[30] Foreign Application Priority Data

Oct. 1, 1975 [DE] Fed. Rep. of Germany ....... 2543722

[51] Int. Cl.² .............................................. C07C 89/54
[52] U.S. Cl. ............................. 560/221; 260/45.85 E
[58] Field of Search .................... 260/486 H; 520/221

[56] References Cited

U.S. PATENT DOCUMENTS 3,763,224  10/1973  Nass et al. ...................... 260/486 H Primary Examiner—Paul J. Killos Attorney, Agent, or Firm—Sprung, Felfe, Horn, Lynch & Kramer

[57] ABSTRACT

Tetrahaloxylene diesters of formulas 1 and 2:

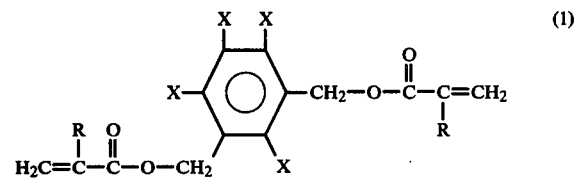

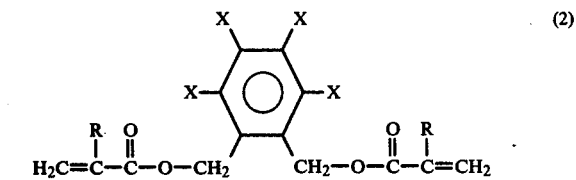

wherein R = hydrogen or a methyl group, and each X is bromo, with the proviso that some of the X's can be chloro. The compounds are useful as flame retardants for plastics.

4 Claims, No Drawings

TETRABROMOXYLYLENE DIACRYLATES AND SUBSTITUTED ACRYLATES

U.S. patent application Ser. No. 589,958, filed June 24, 1975 (Group 127) describes, among other substances, tetrabromo-p-xylylene diacrylate and dimethacrylate as well as a method for the preparation thereof.

It has now been found possible to prepare also tetrahalo-m-xylylene diacrylate and dimethacrylate (structure formula 1) and tetrahalo-o-xylylene diacrylate and dimethacrylate (structure formula 2).

The preparation of the unsaturated esters is accomplished by reacting the meta or ortho isomers of tetrabromoxylylene dichloride with the alkali salts of acrylic acid or methacrylic acid, as the case may be, in polar solvents which are at least to some extent miscible with water.

The subject matter of the present invention is tetrahaloxylylene diesters of Formulas 1 and 2:

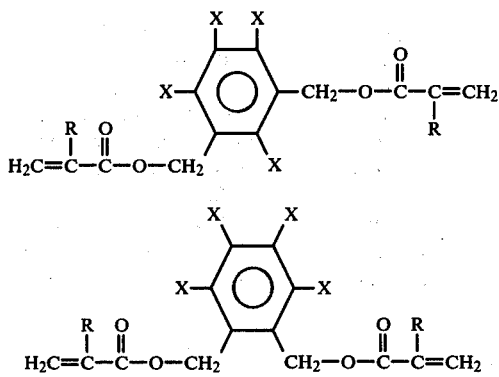

wherein R represents hydrogen or a methyl group.

Also subject matter of the invention is a method of preparing compounds of Formulas 1 and 2 which is characterized in that acrylic acid or methacrylic acid is transformed in a polar solvent to its alkali salts, and then m- or o-tetrabromoxylylene dichloride is transformed to esters of Formulas 1 or 2 at 50° to 150° C., in the presence of a polymerization inhibitor, with a stoichiometric excess of the alkali salt of the acid amounting to from 1 to 10 mole-%.

The starting substances are obtainable by the bromination of the nucleus and chlorination of the side chain of m- or o-xylylene or mixtures thereof, whereupon conventional substances are obtained having bromine only as their nuclear substituent, and yet to some extent substances are also obtained in which a portion of the bromine bound to the aromatic nucleus has been replaced by chlorine, allowance being made for this fact by the use of the substituent X. The chlorine generally amounts to no more than one chlorine atom per molecule, so that m- and o-xylylene bisesters of the sum formula

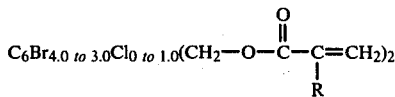

are obtained as the product and are usable in the same manner.

The transposition to the new substances is performed by reaction with acrylic acid or methacrylic acid, as the case may be.

In a polar organic solvent, the unsaturated carboxylic acids are transformed by the addition of, for example, alkali carbonates or bicarbonates or alkali hydroxides or tertiary amines such as triethylamine or tributylamine, to the alkali salts. Of the alkali compounds, the carbonates and the hydroxides are greatly preferred, although the bicarbonates can also be used or, in some cases, the alkali alcoholates, especially the methylates. Then tetrabromoxylylene dichloride is added with the alkali salt of the unsaturated carboxylic acid in a stoichiometric excess of 1 to 10 mole-%, and transposed to the ester at 50° to 150° C., usually in the presence of a polymerization inhibitor.

The formation of salts between (meth)acrylic acid and alkali carbonate or alkali hydroxide, as the case may be, generally takes place in the temperature range from 10 to 80 degrees C., preferably at room temperature, the alkali carbonate being added in portions to the acid in the solvent, after the addition of the polymerization inhibitor, with stirring, so as to prevent excessive foaming (formation of carbon dioxide). If alkali hydroxide is used, it is preferably added in the form of a concentrated aqueous solution. After the tetrabromoxylylene dichloride has been added, the mixture is heated to the reaction temperature ranging from 50° to 150° C., preferably 80° to 130° C., and is allowed to react until the transformation in virtually complete. The reaction time will be from half an hour to five hours. The reaction can be pursued by quantitative determination of the alkali chloride being produced, e.g., by Mohr's method of chloride determination.

Examples of appropriate polar solvents are alcohols of one to four carbon atoms, glycols, ether alcohols, tetrahydrofuran, dioxane, dimethoxyethane, dimethylformamide, dimethylacetamine, N-methylpyrrolidone and dimethylsulfoxide. Ethylene glycol monomethyl ether (methyl glycol) is preferred.

Suitable inhibitors are hydroquinone, p-benzoquinone, pyrocatechol, 4-tert.butylpyrocatechol, hydroquinonemonomethyl ether, 2,4,6-tri-tert.butylphenol. Hydroquinone is used preferentially. $Na_2CO_3$ or $K_2CO_3$ is preferred as alkali carbonate, and NaOH or KOH is preferred as alkali hydroxide.

The stoichiometric excess of 1 to 10 mole-% of the alkali salt of the acid in relation to the tetrabromoxylylene dichloride is intended to assure a complete transformation of the last-named starting products. When the batch is being worked up, it is easy to separate the excess amounts of alkali acrylate or methacrylate together with the alkali chloride that has been formed.

Alkali carbonate or alkali hydroxide and unsaturated acid can be used in amounts that are equivalent to one another; however, for the purpose of avoiding the development of undesired by-products, such as addition products of the ethylene glycol monomethyl ether serving as solvent onto the C═C double bond of the acrylic or methacrylic acid, or polymers which form during the esterification due to vinyl polymerization, it has been found advantageous to use the unsaturated acid in a slight stoichiometric excess with respect to the alkali carbonates used for the salt formation, so that the reaction mixture will have an acid reaction both during and after the salt formation. In this manner the alkali-catalyzed methyl glycol addition onto the acid double bond is prevented and the phenolic inhibitor will exercise an adequate action.

After the end of the reaction, the reaction products, with the exception of the alkali chloride and small amounts of acrylic or methacrylic ester which have polymerized or crosslinked, are in solution. The undissolved products can be separated by filtration or centrifugation. Upon the cooling of the filtrate, the esters of Formulas 1 and 2 crystallize, as a rule, in high yields and sufficient purity. They are separated, washed with water until free of chloride, and dried preferably at room temperature. For the isolation of the esters the reaction solution, after separation, if desired, of substances remaining undissolved in the hot solution, can also be poured into water and the reaction products precipitated in this manner. Such a procedure is especially recommended in the case of tetrabromoxylylene dimethacrylate which crystallizes more sluggishly.

The new substances thus prepared are crystalline substances which are identified by the melting points.

The esters of the invention are usable as reactive crosslinking agents for unsaturated compounds. They have valuable characteristics as flame-inhibiting additives for polymers, in which case they are used as they are or preferably in the form of polymers or copolymers in accordance with the copending patent application Ser. No. 697,190, filed June 17, 1976 (assigned to the assignee hereof). Thus the compounds of the invention can be used in polyethylene for flame inhibition in amounts of 6-12 grams per 100 grams of polyethylene, desirably together with 3-6 grams per 100 grams of polyethylene of antimony trioxide. In addition to having good flameproofing action, the polymers and copolymers are distinguished by their outstanding adherence to the polymers, which is apparently due to polar parts of the molecules and also due to the angling of the polymers and copolymers by organic substituents which link the chain together in the ortho or meta position, as the case may be.

EXAMPLES

Example 1

In a three-necked flask equipped with stirrer and reflux condenser, 18.08 g (0.21 mole) of methacrylic acid and 0.8 g of hydroquinone as polymerization inhibitor are dissolved in 200 ml of methyl glycol, and 8 g of sodium hydroxide (0.2 mole) dissolved in 8 g of water is added all at once to the solution. After the addition of 49.1 g (0.1 mole) of tetrabromo-m-xylylene dichloride, the mixture is heated to 110° C. and let react for 1 hour at 110° C. Mohr's method of chloride determination showed a transformation at 93%. After an additional 30 minutes at 110° C., small amounts of undissolved matter are removed by filtration in the hot state, and the reaction solution is allowed to cool.

A white, crystalline precipitate settled out, which was suction filtered, washed once with methyl glycol, and then washed several times with water. It was then dried in vacuo at room temperature over phosphorus pentoxide until its weight became constant.

The yield amounted to 46 g of tetrabromo-m-xylylene bismethacrylate, which corresponds to 79.9% of the theory. Melting point: 98°-99° C.

Determination of the double bond content by the method of Beesing showed the purity of the bismethacrylate to be 97.2%.

Example 2

11.3 g of anhydrous soda was added to a solution of 15.2 g of acrylic acid and 1.4 g of hydroquinone in 180 ml of methyl glycol, with stirring, at room temperature, in small portions, over a period of 30 minutes.

Then 49.1 g of tetrabromo-m-xylylene dichloride was added and the mixture was heated for 2½ h at 110° C. The reaction mixture was then filtered while hot and let cool in an ice bath.

The crystalline precipitate was suction filtered and washed once with cold methyl glycol and then repeatedly with water. It was dried over phosphorus pentoxide in vacuo at room temperature until its weight became constant.

42.3 g of tetrabromo-m-xylylene bisacrylate was obtained, corresponding to 75.5% of the theory. Melting point: 105°-108° C.

Example 3

8 g (0.2 mole) of sodium hydroxide in solid form (tablets) were added, with stirring, to a solution of 18.08 g (0.21 mole) of methacrylic acid and 1.2 g of hydroquinone in 200 ml of methyl glycol. The sodium hydroxide dissolved at room temperature within 1½ hours, with the formation of salts. 49.1 g (0.1 mole) of tetrabromo-o-xylylene dichloride was added and the reaction mixture was heated at 110° C. After 1½ hours at 110° C., the reaction is stopped, the mixture is filtered while hot, and the filtrate is cooled in the ice bath. The crystalline product in suction filtered, washed once with methyl glycol and several times with water until the filtrate is free of Cl⁻.

After drying to weight consistency, 38.6 g of tetrabromo-o-xylylene bismethacrylate is obtained, which corresponds to 67% of the theory. Melting point: 64°-66° C. Double bond content according to Beesing: 98.1%.

Example 4

By the procedure of Example 3, 34.4 g of tetraboromo-o-xylylenebisacrylate was obtained from the following reaction components in 2 hours of reaction at 110° C.: 15.2 g of acrylic acid, 8 g of sodium hydroxide as salt former in the form of a 50% aqueous solution, 1.2 g of hydroquinone as polymerization inhibitor, 49.2 g of tetrabromo-o-xylylene dichloride, and 200 ml of methyl glycol as solvent; this corresponds to a yield of about 61% of the theory. Melting point: 100°-103° C.

By the addition of water (600 ml) to the mother liquor, a light yellow, highly viscous oil can be isolated which in the subsequent drying solidifies to a horny mass. Yield: 14.3 g, corresponding to 25.5% of the theory. Melting range: 92°-99° C. Double bond content according to Beesing: 91.7%.

We claim:
1. Tetrahaloxylylene diester of formula 1 and tetrahaloxylylene diester of formula 2:

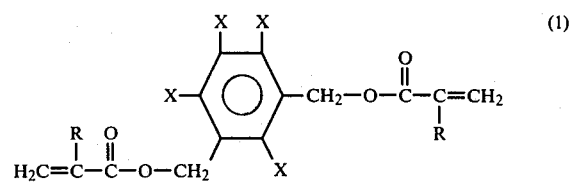

-continued
(2) 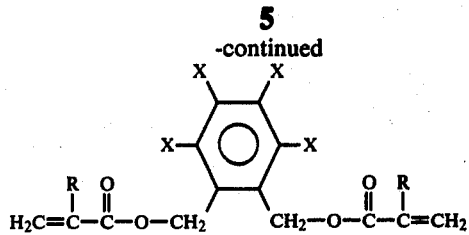
wherein R=hydrogen or a methyl group, and each X is bromo or chloro and at least three of the X's are bromo.
2. Diester of claim 1, wherein each X is bromo.
3. Diester of claim 1, which is of formula 1.
4. Diester of claim 1, which is of formula 2.
* * * * *